(12) United States Patent
Pati et al.

(10) Patent No.: US 6,569,680 B2
(45) Date of Patent: May 27, 2003

(54) EFFICIENT METHOD OF PROTOPLAST CULTURE

(75) Inventors: Pratap Kumar Pati, Himachal Pradesh (IN); Madhu Sharma, Himachal Pradesh (IN); Paramvir Singh Ahuja, Himachal Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/820,556

(22) Filed: Mar. 29, 2001

(65) Prior Publication Data

US 2002/0173037 A1 Nov. 21, 2002

(51) Int. Cl.⁷ .................................................. C12N 5/02
(52) U.S. Cl. ...................... 435/421; 435/420; 435/430.1
(58) Field of Search ................................. 435/421, 425, 435/430.1

(56) References Cited

PUBLICATIONS

Golds et al., J. Plant Physiol., 140:582–587, 1992.*
Kost, et al., J. Exp. Bot. (1995), 46(290), 1157–67.*

* cited by examiner

*Primary Examiner*—Irene Marx
(74) *Attorney, Agent, or Firm*—Mathews, Collins, Shepherd & McKay, P.A.

(57) ABSTRACT

The invention a novel and efficient method for protoplast culture comprising the steps of isolating the protoplasts from a cell suspension, mixing the protoplasts with equal volumes of alginate solution, placing 40–50 $\mu l$ of $CaCl_2$ solution on a glass microslide, placing a mixture of protoplasts and alginate solution on the glass microslide and immediately covering by a glass coverglass, adding $CaCl_2$ solution from the sides of coverglass, sliding down the coverglass towards one side and placing it in a petridish containing protoplast culture medium, sealing the petridishes, incubating it and transferring the extra thin alginate layer with celled colonies to regeneration medium for development of culture.

5 Claims, 1 Drawing Sheet

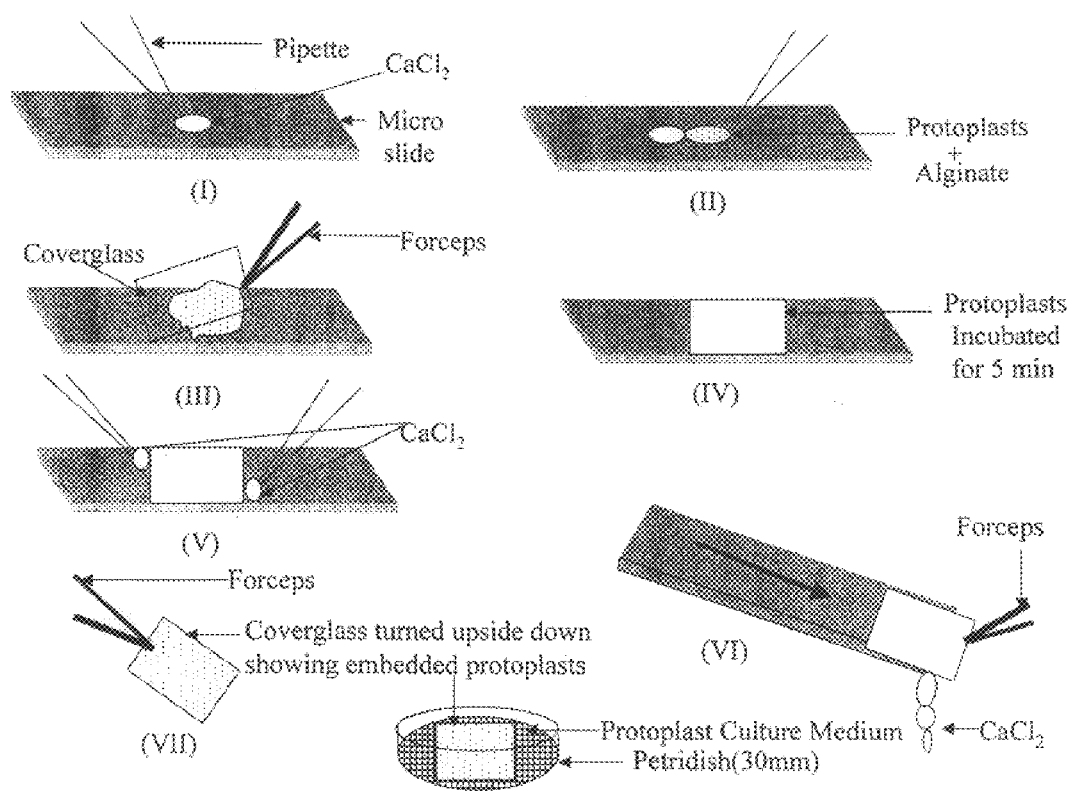
Fig. 1. Extra Thin Alginate Film Technique

EFFICIENT METHOD OF PROTOPLAST CULTURE

FIELD OF THE INVENTION

The present invention relates to an efficient new method of protoplast culture.

BACKGROUND

All organisms, be it plants or animals, reproduce sexually by the fusion of male and female gametes, each containing a single set of chromosomes from either parent and this is possible only in the compatible and related species. Wide crosses are not common without human intervention. However, plant protoplast culture provides a unique system, wherein each protoplast has the potential to give rise to a whole plant and two or more protoplasts can be induced to produce a hybrid (fusion between nuclei) or a cybrid (fusion between cytoplasm of one and the nucleus of another). This technique is used to overcome sexual incompatibility barriers through the production of unique somatic hybrids involving vegetative cells. The lack of cell wall barriers offers significant advantages for the introduction of genetically engineered foreign DNA into the naked cells—that are protoplasts.

Hanstein for the first time used the term protoplast in 1880 (cf. Cocking E. C. 1972. Plant cell protoplasts, isolation and development. Ann. Rev. Plant Physiol. 23: 29–50). The isolation of protoplasts from plant cells was first achieved by Klercker by microsurgery on plasmolysed cells in 1892 (cf. Cocking E. C. 1972. Plant cell protoplasts, isolation and development. Ann. Rev. Plant Physiol. 23: 29–50).). With refinements in the technique, protoplasts were beginning to be isolated in large numbers by enzymatic removal of cell wall as pioneered by Cocking in 1960 (A method for isolation of plant protoplasts and vacuoles. Nature 187: 927). The plant species, condition under which plants are grown, plant age, method of protoplast isolation and protoplast culture are often critical for sustained division of protoplasts. Therefore, there are no standard methods for the isolation and culture of protoplasts. Considerable success has been achieved over the past two decades, when a number of techniques have been employed for the culture of protoplasts of numerous crop species.

In one such method (Binding H. 1974. Cell cluster formation by leaf protoplasts from axenic cultures of haploid *Petunia hybrida* L. Plant Sci. Lett. 2(3): 185–187), the protoplasts at a desired density are suspended in the optimum quantity of liquid medium in a petri dish and incubated at 25–28° C., generally in the dark or diffused light. Such a method provides opportunity to gradually change the osmolarity of the medium for better protoplast growth. But in this method, protoplasts generally tend to aggregate and some even degenerate which adversely affects the dividing protoplasts. This method also suffers from the fact that it requires relatively larger volume of protoplast suspension. Inadequate aeration also adversely affect protoplast growth.

Another method is the hanging/sitting drop culture method (Kao K. N., Keller W. A. and Miller R. A. 1970. Cell division in newly formed cells from protoplasts of soybean. Exp. Cell Res. 62: 338). In this method, small drops (40–100 l) of protoplast suspension are placed on the inner side of the lid of a petri dish so that the drops containing the protoplasts are hanging from the lid. The drops can also be placed at the bottom of the petri dish. Fresh medium can be added in small volumes whenever required. However, this method is generally employed where protoplast yield is low and also requires dexterous handling as a slight shaking disturbs the hanging drop.

Yet another technique used for protoplast culture is the micro-chamber culture method (Bawa S. B. and Torrey J. G. 1971. "Budding" and nuclear division in cultured protoplast of corn, Convolvulus and onion. Bot. Gaz. 132: 420) which is similar to drop culture method except that in this case a cavity microslide or a micro-chamber is used in order to follow the development of individual protoplasts. Here, either a conditioned medium is used or else a feeder layer is required for protoplast growth. However, this method suffers from the defect of quick drying and requires special efforts to ensure aeration.

In yet another method called Micro-drop Array (M.D.A.) technique (Potrykus I., Harms C. T. and Lorz H. 1979. Multiple-drop array (MDA) technique for the large-scale testing of culture media variations in hanging microdrop cultures of single cell systems. 1. The technique. Plant Sci. Lett. 14:231), which is usually employed to test the response of protoplasts to different culture media under varying combinations and permutations. The drop size is reduced to 40 l to accommodate many drops per petri dish. This method provides opportunity to use smaller number of petri dishes. However in this method it is not easy to handle small drops where the size of the drop is too small and it tends to dry quickly.

Another method used is the Micro-droplet Culture Technique (Gleba Y. Y. 1978. Microdroplet cultures: tobacco plants from single mesophyll protoplasts. Naturwissenschaften 65: 158), wherein the size of culture droplet is reduced to about 0.25 to 0.50 l so that each droplet containing only one protoplast is placed separately in numbered wells of special Cuprak petri dishes. However, since only one protoplast is being grown, improved media and pre-culturing of the protoplast is recommended before placing this into micro-culture.

The protoplasts/cells have also been known to be cultured in semisolid media using different gelling agents such as agar, agarose, K-carrageenan, alginate, gelatin and polyacrylamide for secondary metabolite production. In this technique, the protoplast suspension at double the required density is gently mixed with double strength molten agar at 40–45° C. in a petri dish so that protoplasts get embedded in the gel matrix upon solidification. However, a careful monitoring of agar gel temperature needs to be done to avoid damage to the protoplasts because of high temperature. The impurities present in agar also sometimes adversely affect the growth of the protoplasts.

Another method has been the use of semi-solid media using agarose (Lorz H., Larkin P. I., Thomson I. and Scowcroft W. R. 1983. Improved protoplast culture and agarose media. Plant Cell Tissue Org. Cult. 2: 217), wherein the protoplast suspension is made in agarose till micro-calli formation, which is then recovered by remelting the medium at 40° C. But, reheating adversely affects cell growth. An improvement over this method is the use of alginate as the gelling agent (Adaoha-Mbanaso E. N. and Roscoe D. H. 1981. Alginate: an alternative to agar to plant protoplast culture. Plant Sci. Lett. 25: 61), which can then be dissolved in osmotically adjusted sodium citrate solution and the protoplast derived micro-colonies could be easily recovered without affecting the growth. However, another improvement of protoplast regeneration efficiency has been the use of a combination of both semi-solidified blocks/thin layers and liquid media. One such technique is bead culture method, wherein the protoplasts are suspended in agar or agarose. The gel blocks containing embedded protoplasts are transferred to liquid medium and placed on a shaker. In this manner, an improvement in the protoplast growth could be accomplished but again, this method is quite cumbersome and involves many steps. Out of all gelling agents, use of agarose has improved protoplast culture efficiency and also the production of secondary metabolites, when protoplasts are embedded in thin layers of agarose placed on top of the solidified medium in a petri dish. However, the cost and the handling of agarose is a major constraint. Moreover, the recovery of micro-colonies is difficult in the embedding procedure using agar or agarose as it requires heating and remelting of agar/agarose which may adversely affect the growth of protoplasts.

An improvement over all the methods described above is the the Thin Alginate Layer (TAL) technique (Golds T. J., Babezinsky J., Rauscher G. and Koop H. U. 1992. Computer controlled tracking of single cell development in *Nicotiana tabaccum* L. and *Hordeum vulgare* L. Protoplasts embedded in agarose/alginate films. J. Plant Physiol. 140: 582–587). This technique encompasses several positive points over earlier methods and was used for Nicotiana mesophyll protoplasts. In this method, squares of polypropylene mesh (2.0×2.0 mm grid) are cut so that it exactly fits into 60 mm petridish. Protoplasts at twice the required density in MMM550 are suspended in equal volumes of 2.8% (w/v) alginic acid to give final alginate concentration of 1.4%. For one grid preparation, 625 $\mu$l of this mixture is placed on an agar layer (20 mM $CaCl_2$), and a polypropylene mesh (10×10 meshes; 2.0×2.0 mm mesh size) is placed over it. After one hour, the grid is slid gently towards one side and taken out. This is then placed upside down in a 60 mm petri dish containing 10 ml of protoplast culture medium. Excess of calcium chloride is removed by giving two washings with protoplast culture medium (10 ml) and finally cultured in 2.0 ml of the same medium. These are then incubated in dark/diffused light at 25° C. The protoplasts divide to form colonies. When colonies of 10–20 celled stage are formed, these are transferred to regeneration medium. Despite the fact that TAL technique has certain advantages like cell tracking, convenience in transfer to fresh medium, reduced release of toxic substances to the medium, it has certain limitations like i) This process is time consuming and costly
ii) When grid is transferred to regeneration medium, callus or differentiated tissue sometimes folds upwards and ultimately slips out of grid, thereby loosing contact with the medium.
iii) The alginate layer is thick, hence protoplasts in multilayers are difficult to track.
iv) The use of a specific polypropylene mesh which is not easily available.

As seen above, all the methods described suffer from one or the other limitations, therefore, an improvement over TAL technique is the presently proposed Extra Thin Alginate Film (ETAF) technique.

Extra Thin Alginate Film Technique as compared to TAL technique is simpler to perform, less time consuming and economical. The advantages of this technique can be enumerated as follows:

a. It is less expensive than TAL technique as
   agar component of $CaCl_2$ is eliminated (25 ml of gelled $CaCl_2$ medium is poured into petriplates where two grids can be prepared. For 25 ml of medium 200 mg of agar is used. Therefore for one grid 100 mg of agar is required).

Only 150 $\mu$l of $CaCl_2$ solution is required instead of 25 ml of $CaCl_2$ medium. Similarly, for one coverglass only 50 $\mu$l of Alginate is required.

Microslides and coverglass are less expensive, can be reused and are easily available throughout the world than the polypropylene grid.

Protoplast culture medium required for washing is just one ml for each washing compared to 10 ml in TAL technique.

This technique also saves time as compared to TAL technique as complexation time is only 5 minutes compared to one hour, Two washings of 15 minutes each are required instead of two washings for 30 minutes, preparation of grid (sizing, autoclaving and drying) consumes a lot of time, whereas microslide and coverglass can be sterilized after giving a dip in alcohol and by subsequent flaming, e. Protoplasts are evenly spread and easy to track due to ultra thin layer,
f. While using TAL technique, callus or differentiated tissue sometimes folds upwards and ultimately slips out of the grid thereby loosing contact with the medium. However, in the present proposed ETAF technique none of these limitations prevail.
g. While performing fusion experiments on coverglasss, the protoplasts can be easily embedded using this technique.

Thus the present invention overcomes the limitations of all the protoplast culture techniques described so far.

OBJECTS OF THE INVENTION

The main objective of the present invention is to provide an efficient new method of protoplast culture.

Another objective of the present invention is to provide an extra thin embedding layer so that protoplasts are evenly spread for ease in observation and tracking for the purpose of plant genetic manipulations, particularly somatic cell hybridization, cybridization and transgenics.

Still another objective of the present invention is to simplify the procedure by using easily available merchandise such as glass microslides and coverglass and also to increase its universal appeal.

Yet another objective of the present invention is to reduce the cost factor involved and the time taken in protoplast culture.

DETAILED DESCRIPTION OF VARIOUS ILLUSTRATIVE EMBODIMENTS

Accordingly the present invention provides an efficient method for protoplast culture, which comprises the steps of:
a) isolating the protoplasts from a cell suspension,
b) mixing the protoplasts with equal volumes of alginate solution,
c) placing 40–50 $\mu$l of $CaCl_2$ solution on a clean glass microslide,
d) placing a mixture of protoplasts and alginate solution on the glass microslide and immediately covering by a glass coverglass,
e) adding $CaCl_2$ solution in an amount of 70 to 100 $\mu$l from the sides of coverglass,
f) sliding down of coverglass towards one side after four to ten minutes, with the help of jewellers forceps and placing in a petridish (Cell Culture Dish, 35×10 mm w/2 mm grid; Genetix, USA, Cat. No. 174926) containing one ml of protoplast culture medium, g) sealing of petridishes with parafilm and incubating in dark/diffused light at 20 to 27° C., and h) transferring of Extra Thin Alginate Layer with 20–25 celled colonies to regeneration medium.

In an embodiment, rose (*Rosa damascena*) protoplasts from cell suspension were used.

In another embodiment, mesophyll protoplasts of *Nicotiana tobacum* cv. Petit Havana were used.

In yet another embodiment, cotyledon protoplasts of *Lotus corniculatus* were used.

In still another embodiment, the regeneration medium is modified MS medium supplemented with 0.1 mg/l Benzyl amino-purine and Naphthalene acetic acid 0.01 mg/l in nicotine.

In yet another embodiment, 40–50 μl of $CaCl_2$ solution is placed on a clean glass microslide.

In still another embodiment, mixture of protoplasts and alginate is placed on drop of $CaCl_2$ and is immediately covered by a clean coverglass.

In yet another embodiment, more of $CaCl_2$ solution is added from the sides of coverglass.

In yet another embodiment, the coverglass is gently slided down towards one side with the help of jewellers forceps.

The technique described in the invention can be performed by less expensive easily available material, wherein the callus or differentiated tissue remains constantly in touch with the nutritive medium and due to the extra thin layer, protoplasts are seen in one focus and are easy to track.

The advantages of the method of the invention over the prior art methods are provided hereinbelow and illustrated in FIG. 1 of the accompanying drawings.

TABLE 1

| Thin Alignate Layer (TAL) Technique (Golds et al. 1992) | Extra Thin Alignate Film (ETAF) Technique |
|---|---|
| 1. 20–25 ml of agar gelled $CaCl_2$ medium is required. | 1. Only 120–150 μl of $CaCl_2$ without agar is required. |
| 2. For one grid 325 μl of sodium alginate is required. | 2. For one coverglass only 40–50 μl of sodium alginate is required. |
| 3. Polypropyline grid is not easily available. | 3. Micro-slides and coverglass are less expensive, can be required and are easily available. |
| 4. Medium required for washing of grid is 10 ml. | 4. Medium required for ETAF is just one ml. |
| 5. Complexation time for alginate is one hour. | 5. Complexation time for alginate is 5–7 minutes. |
| 6. Preparation of grid (sizing, autoclaving and drying) consumes a lot of time. | 6. Microslide and coverglass can be sterilized after giving a dip in alcohol and subsequent flaming. |
| 7. Callus or differentiated tissue folds upwards thereby losing contact with the medium. | 7. Callus or differentiated tissue folds upwards thereby losing contact with the medium. |
| 8. Cell tracking possible but protoplasts are in 2–3 foci. | 8. While performing fusion experiments on coverglass, the protoplasts can be easily embedded using this technique. |
| | 10. Due to extra thin layer, protoplasts are seen in one focus hence easy to look. |
| | 11. We got the idea while doing fusion experiments on coverglass. |

The technique described can be performed by less expensive, easily available material, wherein the callus or differentiated tissue remains constantly in touch with the nutrition medium and due to extra thin layer protoplasts are seen in one focus and are easy to look.

The following examples are given by way of illustration of the present invention and should not be construed to limit the scope of present invention.

EXAMPLE-1

In rose, protoplasts were isolated from actively growing cell suspension in exponential phase (7–8 days after subculture) in fresh Murashige and Skoog (MS) medium (Murashige T. and Skoog F. 1962. A revised medium for rapid growth and bioassays with tobacco tissue cultures. Physiologia Plantarum 15: 473–497) containing 6-benzylamino purine (BAP) and 2,4-dichlorophenoxy acetic acid (2,4-D) (5 μM each). The cell culture medium was decanted and the cells plasmolysed in a plasmolysing solution i.e., CPW 13M (Cell and Protoplast Washing salt solution with 13% mannitol) for one hour. Later on, CPW was replaced by an enzyme mixture (Cellulase R10, Onozuka, Yakult Honsha, Japan, 1.0–5.0%; Macerozyme R10, Onozuka, Yakult Honsha, Japan, 0.25–1.0%; and Driselase (Sigma, USA, 0.25–1.0%) and incubated at 25° C. in dark on a shaker (60 rpm) for 14–16 hours. After incubation, protoplasts and partly digested cells were passed through a sieve (90 μm pore size) with undigested tissues being rinsed with 10 ml of CPW 13M solution. The filtrate containing protoplasts was centrifuged (80 g) for 10 minutes and the supernatant was discarded. For purification, protoplasts were suspended in high density sucrose solution i.e., CPW 21S (CPW with 21% sucrose) and centrifuged (100 g) for 10 minutes. Protoplasts free of debris were carefully removed from the interface of the solutions and resuspended in known volume of MMM550 ($MgSO_4.7H_2O$, 1.69 g/l; $MgCl_2.6H_2O$, 2.3 g/l; MES 1.95 g/l; Mannitol, 130 g/l). Protoplasts could be counted at this stage. When protoplasts were cultured at a plating density of $4\times10^5$ protoplasts/ml in modified MS medium (see table 1) the first division was observed on day 1 and 8–10 celled colony stage was observed within a week. In 2 weeks, 30–40 celled colonies were formed and could be transferred to regenerating medium. A plating efficiency of 71.4% was recorded after 10 days of culture.

EXAMPLE-2

Seeds of *Nicotiana tobacum* cv. Petit Havana were soaked in water for 2 hours. These were surface sterilized in 2.0% (w/v) calcium hypochlorite solution for 20–25 minutes and repeatedly washed in sterilized distilled water in order to remove the traces of sterilizing agent. These were inoculated in 100 ml Erlenmeyer flasks containing MS medium+ sucrose 2.0%+agar 0.8%. After about a week, the roots of seedlings were excised and shoots were transferred one each in bigger culture vessels. Fully expanded leaves (3rd or 4th) from these cultures were taken for protoplast isolation. A leaf was placed on a ceramic tile with its abaxial side up. After having removed the midrib, either epidermis was peeled off or the leaf sliced into small pieces. These leaf pieces (abaxial side down) were transferred to a petridish containing 9 ml of protoplast isolation medium and 0.5 ml each of cellulase R10 and macerozyme 1% enzyme stock solution in sucrose. The dishes were sealed and incubated overnight (16–18 hours) in the dark at 25° C. Protoplast suspension and undigested leaf material was then passed through a 90 μm sieve into an autoclaved petridish. The protoplast suspension was centrifuged at 100 g for 10 minutes. The protoplasts were collected in the form of a green band at the surface and were carefully removed into a tube to which MMM550 was added. Protoplasts were pelleted by centrifugation at 80 g for 5 minutes. Supernatant was removed and a known volume of MMM550 solution was added so that desired density could be adjusted. Protoplasts were cultured at a plating density of $1\times10^5$ protoplasts/ml in modified MS medium containing BAP (1 mg/l) and α-naphthalene acetic acid (NAA, 0.1 mg/l). First division occurred on day one and after two weeks, visible callus was transferred to regeneration medium (modified MS supplemented with BAP (0.1 mg/l) and NAA (0.01 mg/l). Shoot regeneration was observed after 4 weeks of isolation.

EXAMPLE-3

Seeds of Lotus corniculatus were surface sterilized using 0.04% (v/v) sodium hypochlorite containing 0.2% (v/v) tween 80 (Himedia, Mumbai) for 20 minutes on a gyratory shaker. The solution was decanted and next step of surface sterilization was carried out in a laminar flow cabinet using 0.04% (w/v) mercuric chloride solution to which 1–2 drops of Tween 80 were added as a wetting agent. After 6–7 minutes, the mercuric chloride solution was decanted and seeds repeatedly washed with sterilized distilled water to remove all traces of sterilizing agent. Seeds were germinated on agar (0.8%) gelled Murashige and Skoog (1962) medium containing 3% sucrose but lacking growth regulators, and incubated in the dark at 23±2° C. Cotyledons were excised from 2–7 days old aseptic seedlings maintained at 4° C. for 48 hours in the dark prior to use. The cotyledon slices were chopped into small pieces and put in a plasmolytic solution i.e. CPW 13M for one hour which was later replaced by an enzyme mixture (1–2.0% Cellulase R10, 0.25–0.5%; Macerozyme R10 and 0.25–0.5% Driselase) and incubated at 28° C. in dark without agitation. Protoplasts were released by gently squeezing the material. Protoplasts were passed successively through nylon sieve of pore size 64 $\mu$m and 20 $\mu$m and pelleted by centrifugation (80 g for 5 minutes). Protoplasts were washed twice in MMM550 salt solution. Protoplasts were cultured at a plating density of $2 \times 10^5$ protoplasts/ml. First division occurred on day 2 and visible callus formed after two weeks, which was transferred to regeneration medium [MS supplemented with BAP (2.5 $\mu$M) and MS basal medium]. Shoots emerged after 2 weeks.

In view of the foregoing description, numerous modifications and alternative embodiments of the invention will be apparent to those skilled in the art. Accordingly, this description is to be construed as illustrative only and is for the purpose of teaching those skilled in the art the best mode of carrying out the invention. Details of the structure may be varied substantially without departing from the spirit of the invention, and the exclusive use of all modifications, which come within the scope of the appended claim, is reserved.

We claim:

1. An efficient method for protoplast culture which comprises the steps of in order:

a) Isolating protoplasts from a cell suspension,
   b) suspending the protoplasts in an equal volume of an about 2.8 w/v alginate solution,
   c) placing 40–50 $\mu$l of an about 20 mM $CaCl_2$ solution on a clean glass microslide,
   d) placing a mixture of protoplasts and alginate solution on the microslide and immediately covering by a coverglass,
   e) further adding $CaCl_2$ solution in an amount of 70 to 100 $\mu$l from the sides of the coverglass,
   (f) sliding down the coverglass towards one side after four to ten minutes and placing said coverglass and a resulting extra thin alginate layer in a petridish containing protoplast culture medium,
   g) sealing the petridish with parafilm and incubating at 20 to 27° C., and
   h) transferring the extra thin alginate layer with 20–25 celled colonies to regeneration medium for development of callus or differentiated tissue.

2. A method as claimed in claim 1 wherein the protoplasts are selected from the group consisting of Rosa damascena, Nicotiana tabacum, and Lotus corniculatus.

3. A method as claimed in claim 1 wherein the regeneration medium is modified Murashige and Skoog medium supplemented with 0.1 mg/l Benzyl amino-purine and Naphthalene acetic acid 0.01 mg/l.

4. A method as claimed in claim 1 wherein the callus or differentiated tissue remains constantly in touch with the regeneration medium.

5. A method as claimed in claim 1 wherein step f) the coverglass with extra thin alginate layer is placed upside down in a 30 mm petridish containing one ml of protoplast culture medium.

* * * * *